US006935338B1

(12) United States Patent
Triunfo, Jr.

(10) Patent No.: US 6,935,338 B1
(45) Date of Patent: Aug. 30, 2005

(54) FLUID RESISTANT AIRWAY ADAPTER

(75) Inventor: John A. Triunfo, Jr., Fairfield, CT (US)

(73) Assignee: RIC Investments, Inc., Wilmington, DE (US)

( * ) Notice: Subject to any disclaimer, the term of this patent is extended or adjusted under 35 U.S.C. 154(b) by 0 days.

(21) Appl. No.: 10/790,321

(22) Filed: Mar. 1, 2004

(51) Int. Cl.$^7$ ...................... A61M 16/00; G01N 19/00; G01F 1/34; G01F 1/37
(52) U.S. Cl. ......................... 128/204.22; 128/204.23; 600/529; 600/531; 600/532; 73/23.2; 73/861.42; 73/861.52; 73/861.63
(58) Field of Search ...................... 128/204.23, 205.12, 128/205.23, 204.22; 600/531–533, 538, 476, 600/477, 529; 73/23.2, 23.3, 23.35, 23.36, 73/23.27, 23.41, 861.42, 861.52, 861.63

(56) References Cited

U.S. PATENT DOCUMENTS

| | | | |
|---|---|---|---|
| 4,177,381 A | | 12/1979 | McClatchie et al. |
| 4,692,621 A | | 9/1987 | Passaro et al. |
| 5,153,436 A | * | 10/1992 | Apperson et al. ........... 250/345 |
| 5,379,650 A | * | 1/1995 | Kofoed et al. ............ 73/861.52 |
| 5,789,660 A | * | 8/1998 | Kofoed et al. ............... 73/23.2 |
| 6,095,986 A | * | 8/2000 | Braig et al. ................. 600/532 |
| 6,142,148 A | * | 11/2000 | Weckstrom et al. ... 128/204.22 |
| 6,216,692 B1 | * | 4/2001 | Todokoro et al. ...... 128/205.23 |
| 2003/0191405 A1 | | 10/2003 | Rich et al. |

* cited by examiner

Primary Examiner—Teena Mitchell
(74) Attorney, Agent, or Firm—Michael W. Haas (57) ABSTRACT

An airway adaptor that includes a tubular body having a first gas flow passage defined therein. A protrusion extends from an interior wall of the tubular body into the gas flow passage. The protrusion includes a distal end portion spaced apart from the interior wall of the tubular body, and a second gas flow passage defined through the protrusion. An inlet to the second gas flow passage is provided at the distal end portion of the protrusion, and an outlet of the second gas flow passage is provided at an exterior portion of the tubular body. A pair of sidewalls are disposed on the distal end portion of the protrusion. Each sidewall is generally parallel to a direction of a flow of gas through the first passage. The inlet of the second gas flow passage is disposed between the pair of sidewalls.

19 Claims, 6 Drawing Sheets

FLUID RESISTANT AIRWAY ADAPTER

BACKGROUND OF THE INVENTION

1. Field of the Invention

The present invention pertains to an airway adapter for use with a sidestream gas sampling system, and, in particular, to an airway adapter with a single port that is substantially less sensitive to the ingress of fluids into the sidestream gas sampling system, regardless of the orientation of the port, than conventional airway adapters.

2. Description of the Related Art

Respiratory gas measurement systems are widely used in medical applications and are typically categorized by operating modality into two different types: (1) "diverting" or "sidestream" gas sampling systems; and (2) "non-diverting" or "mainstream" gas sampling systems. A diverting gas measurement system transports a portion of the sampled gases from a sampling site, through a sampling tube, to a gas sensing system. A path (usually optical) is provided through the flow of sample gas to permit the constituents of the gas to be measured by the gas sensing system. Typically, a sample cell is provided at the end of the sampling tube distal from the sampling site. The optical path is provided by means of a window, or pair of windows, disposed on a wall of the sample cell, so that light or other radiant energy passes into to sample cell through the window and travels through the flow of gas in the sample cell to measure the constituents of the gas in the sample cell. The gas sensing system typically includes a radiation emitter, which transmits radiation, such as light, through at least a portion of the gas flow, and a detector, which measures the radiation passing through that portion of the sample gas flow.

A non-diverting gas measurement system does not transport gas away from the sampling site, but measures the gas constituents at the gas sample site, e.g., directly at the patient circuit. This is accomplished by locating the gas sensing system directly on the patient circuit using an appropriate adapter. While mainstream gas measurement systems generally offer better performance because they offer a more direct measurement of the gas constituents, sidestream gas measurement systems have been considered to be better suited for some clinical applications.

For patients receiving ventilatory support, a patient circuit communicates a flow of gas between the ventilator or other pressure support system and the airway of the patient. A patient interface device is provided at the distal end of the patient circuit to communicate the gas from the patient circuit to the patient's airway. A wide variety of different types of patient interface device are known, such as an endotracheal tube, tracheomy tube, or mask. An airway adapter is used to provide access to the respiratory gas of the patient. The airway adapter is disposed in the patient circuit so that gas delivered to and received from the patient passes through the adapter. Gas is drawn from the patient circuit to the sidestream gas sampling system by means of a sampling port provided in the airway adapter. Thus, the airway adapter provides the sampling site from which gas is extracted for measuring its constituents.

With diverting gas measurement systems, a portion of the gas flow is drawn from the patient circuit through at least one port provided in the airway adapter, transported through the sampling tube, and then analyzed by the gas sensing system. In some conventional diverting gas measurement systems, a filter/water trap is located along the gas flow path, typically upstream of the gas sensing system, to prevent water or other contaminants from entering the gas sensing system.

In some conventional airway adapters, the inlet portion of the port from which the gas sample is drawn projects from the wall of the airway adapter. This allows the gas sample to be taken from the central portion of the gas flow in the patient circuit. It is also known to provide the inlet portion of the port in the airway adapter flush with the wall of the adapter. It is further known to provide the outlet portion of the port in a conventional airway adapter such that it projects from the outer wall of the adapter. This projection is used couple the sampling tube to the port. On the other hand, it is also known to provide a recess in the exposed wall of the airway adapter to which the sampling tube connects.

The measurement of the partial pressure of a gas significantly distant from the sampling site requires consideration of several issues: including (1) how to minimize the ingress of contaminants into the sampling tube, (2) what portion of the gas stream is being sampled, and (3) what configuration for the structure used take the gas sample from the gas flow should have.

Airway adapters are typically located as close to the patient's airway as possible in order to minimize the mixing and resulting dampening of the gas waveform that would occur by placing the airway adapter farther downstream from the patient. By placing the airway adapter close to the airway, the humidity of the gas is near 100% RH, and condensation is likely to occur, resulting in water droplets on the interior surface of the airway adapter. Additionally, substances, such as liquid or solid secretions, or mixtures thereof, including mucous, saliva, blood, and condensed water may be present and potentially block or clog the sampling system. The ingress of such substances into the sidestream gas sampling system degrades the performance of the sidestream system and dramatically reduces the lifetime of the sampling tube/filter set.

Because sidestream gas sampling systems divert gas from the gas stream for analysis, it is clinically desirable to minimize the volume of gas that is removed from the gas stream, particularly for patient groups such as infants and neonates, which have relatively small tidal volumes. Therefore, the typical sampling flow rate of 150–180 ml/min is decreased to 50 ml/min for such patients. Additionally, in an intubated patient, airway adapters may be directly connected to the endotracheal tube connector or connected via an elbow or located elsewhere in the breathing circuit. With a direct endotracheal tube connection, a jetting effect may occur with the gas stream being primary centrally located within the airway adapter. With an elbow connection, the gas velocity profile is asymmetric. Therefore, careful consideration of how and where the gas sample is drawn is important to ensure that the sidestream waveform measurement retains as much fidelity as possible.

One approach to reduce the susceptibility to the ingress of liquid is the placement of multiple inlet ports within the gas stream. If one port inlet becomes occluded, the other(s) could continue to draw gas to the sampling system. However, such multiple port designs are complicated and draw air from different portions of the gas stream depending upon the nature and location of the occlusion.

The inlet ports of in conventional sidestream sampling airway adapters also require that the port be placed in a substantially upright position, thereby utilizing gravity to help prevent fluids from entering the sampling system. However, requiring clinical users to maintain the airway adapter in an upright position is frequently unrealistic in today's resource-limited hospital environment. Additionally, the airway adaptor may be incorrectly installed by clinical personnel, and patient movement may cause the airway adapter and its port to rotate, thereby requiring that the adapter be frequently repositioned. Thus, an airway adapter having an inlet port that is insensitive to position so that its orientation need not pay a significant role in the connection of the airway adapter in the patient circuit, would be highly desirable and would reduce the need to reposition the airway adapter.

Therefore, there is a need for an airway adapter with an inlet that is preferably centrally positioned within the airway adapter, relatively insusceptible to the ingress of substances into the sampling system to which the airway adapter is connected, position/orientation independent, and having a design that is inexpensive to manufacture.

SUMMARY OF THE INVENTION

Accordingly, it is an object of the present invention to provide an airway adapter for sidestream gas sampling that overcomes the shortcomings of conventional airway adapters. This object is achieved by providing an airway adapter that includes a tubular body having a first gas flow passage defined therein, and a protrusion extending from an interior wall of the tubular body into the gas flow passage. The protrusion includes a distal end portion that is spaced apart from the interior wall of the tubular body. A second gas flow passage is defined in the protrusion. An inlet to the second gas flow passage is provided at the distal end portion of the protrusion, and an outlet is located at an exterior portion of the tubular body, so that gas sampling conduit can be connected to the airway adapter to carry a flow of gas to the gas measurement system. A pair of sidewalls are disposed on the distal end portion of the protrusion. Each sidewall is generally parallel to a direction of a flow of gas through the first passage. The inlet of the second gas flow passage is disposed between the pair of sidewalls.

By providing an airway adapter having such a configuration, the present invention prevents or reduces the ingress of liquids into the gas sampling conduit regardless of the orientation of the airway adapter. The sidewalls coupled to the protrusion present a U-shaped profile to the gas passing through the airway adapter, where the sidewall defining the sides of the "U" are generally parallel to the direction of flow in the airway adapter. This configuration minimizes the resistance for the flow of gas through the airway adapter, i.e., minimize the pressure drop through the adapter.

Further features of the present invention include tapering the inside walls of the "U" such that they taper outward from the inlet of the second gas flow passage. In addition, a small protrusion is positioned around the inlet opening at the base of the "U" to further enhance resistance to fluid ingress into the inlet of the second gas flow passage. Sharp corners on the protrusion are preferred and beneficial in wicking away fluid droplets. The protrusion is also located substantially within the tubular body and is substantially perpendicular to the wall of the tubular body. The portion of the protrusion defining the inlet to the second gas flow passage is also preferably formed from material that is substantially hydrophobic, to help prevent accumulation of droplets on the surface of the inlet portion of the second gas flow passage.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
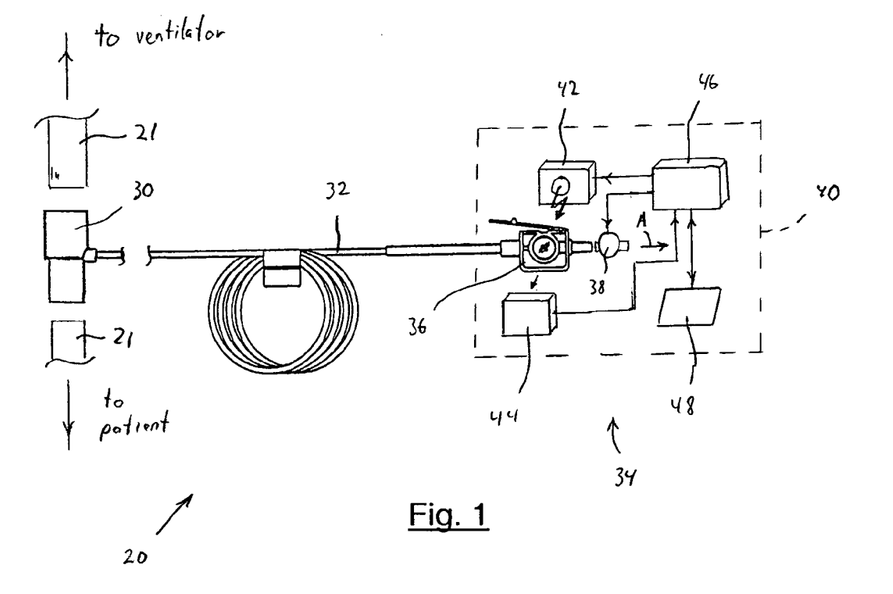
FIG. 1 is a schematic diagram of a sidestream gas sampling system that is capable of using the airway adapter of the present invention.

FIG. 1 illustrates a sidestream gas sampling system 20 that uses an airway adapter 30 according to the principles of the present invention. Airway adapter 30 in sampling system 20 is connected in-line in a breathing circuit 21, also referred to as a patient circuit, so that gas passing to and from the patient travels through the airway adapter. A gas sampling conduit 32, which is a small bore tubing connected to the airway adapter, transports gas picked off from the gas flow in the patient circuit at the airway adapter to a gas measurement system 34. Various embodiments for airway adapter 30 are described below with reference to FIGS. 2–14. The airway adapter described in each of these embodiments is suitable for use as airway adapter 30.

During operation, gas measurement system 34 aspirates a flow of sample gas from the breathing circuit via airway adapter 30 through gas sampling conduit 32, as indicated by arrow A. In the illustrated embodiment, the flow of sample gas enters a sample cell 36 at sample flow rates ranging from 50 to 250 ml/min. A pump 38 is provided in gas measurement system 34 to draw the gas into the sample cell from the gas sample site. Pump 38 is preferably located downstream of the sample cell to pull the flow of sample gas from the patient circuit through the sample cell.

Gas measurement system 34 also includes the components necessary to measure the concentration of a gas constituents in the flow of sample gas in the sample cell. For example, gas measurement system 34 includes a radiation emitting source 42 that is configured and arranged to emit radiant energy into the sample cell, for example through a window provided in the sample cell. A photodetector 44 receives the radian energy after having passed through the gas in the sample cell and produces a signal indicative of the concentration of a gas constituents in the flow of sample gas based on the energy passing through the gas sample in the sample cell. A processing system 46 converts the detected signal from the photodetector into a value used to produce an indication of the concentration of a particular gas constituent. An input/output device 48 is provided to display, communicate, or otherwise transmit the results to other devices, such as a database, printer, or monitor, and to allow the user to input information to the gas measurement system. The components of the gas measurement system are typically contained in a housing 40, which is typically a stand-alone unit or a module in a larger system, such as a ventilator or multi-parameter monitoring system.

An example of a sidestream gas sampling system suitable for use with the airway adapter of the present invention is described in published U.S. patent application Ser. No. 10/384,329 filed Mar. 7, 2003 (Publication No. 2003/0191405, published Oct. 9, 2003), entitled, "Sidestream Gas Sampling System with Detachable Sample Cell," the contents of which are incorporated herein by reference. Other examples of conventional sidestream gas measurement systems are taught in U.S. Pat. No. 4,692,621 to Passaro et al.; U.S. Pat. No. 4,177,381 to McClatchie, and U.S. Pat. No. 5,282,473 to Braig et al. It is to be understood that the airway adapter of the present invention is suitable for use with these or any other conventional sidestream gas sampling system.

The details of a first embodiment of an airway adapter 100 suitable for use as airway adapter 30 in a sidestream gas sampling system are discussed below with reference to FIGS. 2–6. Airway adapter 100, in this embodiment, is a two-component pediatric/adult airway adapter, which is comprised of a tubular body 120 and an insert 110. A distal end portion 118 of the insert defines a protrusion that extends into an interior of the tubular body.

Figure 2:
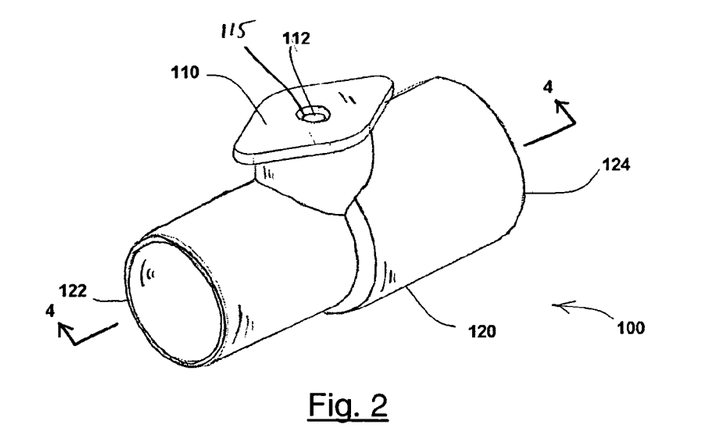
FIG. 2 is a perspective view of a two component pediatric/adult airway adapter according to the principles of the present invention.

A first end portion 122 of tubular body 120 is sized and configured to connect to a Y-connector in a ventilator circuit, and a second end portion 124 of the tubular body is sized and configured to connect to an endotracheal tube connector. It is to be understood that end portions 122 and 124 can be connected to other portions of the patient circuit or to other components. It is preferable, however, in conventional capnography systems, for the airway adapter to be positioned as close to the patient as possible. A first gas flow passage 125 is defined through the tubular body between first and second end portions 122 and 124.

Figure 4:
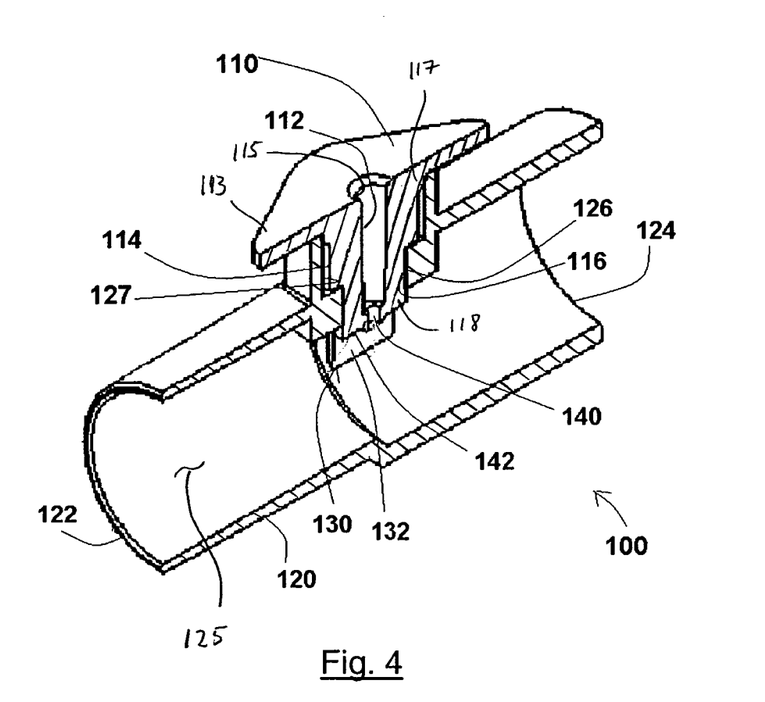
FIG. 4 is a cross-sectional perspective view of the pediatric/adult airway adapter taken along line 4—4 of FIG. 2.

In the illustrated embodiment, insert 110 is mounted within an aperture defined through a wall of tubular body 120 such that distal end portion 118 of the insert is spaced apart from the interior wall of the tubular body. In addition, the protrusion formed by the insert is substantially centrally located on the tubular body and extends into first gas flow passage 125 in a direction that is substantially perpendicular to the interior wall of the tubular body, i.e., perpendicular to a gas flow path through the tubular body.

Although insert 110 can be coupled to the tubular body using any conventional technique, an exemplary embodiment of the present invention contemplates attaching the insert to the tubular body by means of a threaded coupling. To this end, insert 110 includes a threaded cylindrical surface 114 that engages a corresponding threaded cylindrical surface 127 on an interior of the aperture. The threaded engagement between insert 110 and tubular body 120 provides a good seal between these two components and also consistently positions distal end portion 118 of the protrusion within the gas stream that flow through tubular body 120.

A cylindrical surface 116 of insert 110 mates with a corresponding cylindrical surface 126 of tubular body 120. A second gas flow passage 112 is defined through insert 110. A first opening 115 to the second gas flow passage is provided in a proximate end portion 117 of the insert at an exterior portion of the tubular body. A second opening 140 to the second gas flow passage is provided at distal end portion 118 of insert 110. A flange 113 is provided at the proximal end of the insert.

Figure 3:
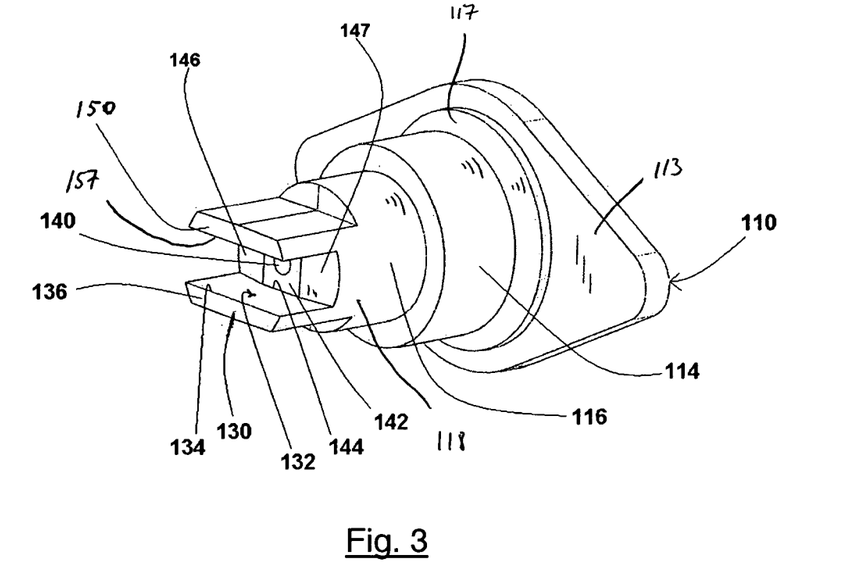
FIG. 3 is a perspective view of the protrusion in the airway adapter of FIG. 2.

A pair of sidewalls 130 and 150 are disposed on distal end portion 118 of insert 110 such that each sidewall is generally parallel to a direction of a flow of gas through first gas flow passage 125. Second opening 140, which serves as an inlet for second gas flow passage 112, is disposed between the pair of sidewalls. Sidewalls 130 and 150 are positioned substantially parallel to the direction of flow such that the sidewalls form a U-shaped channel 128 when viewed in the direction of gas flow, i.e., in a direction generally parallel to a longitudinal axis of tubular body 120. The profile of the sidewalls that are normal to the direction of flow is minimized to keep the flow resistance low. In other words, the thickness and/or the aerodynamics of the sidewalls are selected to minimize the resistance to flow through the tubular body caused by the presence of the sidewalls in the gas flow path. Sidewalls 130 and 150 include lateral surfaces 132 and 151, respectively, that face one another and define the walls of the U-shaped channel.

As perhaps best shown in FIGS. 3–6, opening 140 is defined in a surface 142 at distal end portion 118 of the insert. In an exemplary embodiment of the present invention, opening 140 provides access to a narrow bore 133 that is coupled to a wide bore 135. Thus, second gas flow passage 112 is defined by narrow bore 133 and wide bore portion 135. Surface 142 at the distal end of the insert includes a central planar surface 145, a first inclined surface portion 146, and a second inclined surface portion 147. Inclined surfaces 146 and 147 are located on opposite sides of central planar surface 145.

The junction between each lateral surface 132 and 151 of sidewalls 130 and 150 and surface 145, which surrounds opening 140, is preferably a sharp edge. The sharp edge at these junctions provide the means to wick away water droplets and other accumulations in the normal upright position. FIG. 3 illustrates a junction 144 between lateral surface 132 and surface 142 where the sharp is provided.

Opening 140 should be sufficiently large to permit an adequate flow of sidestream of gas for sampling, yet is sufficiently small to encourage production of a surface tension of a fluid on the opening, thereby discouraging entry by liquids or mixtures containing liquids, such as mucous and saliva. Additionally, inclined surfaces 146 and 147, which are located on the sides of substantially planar surface 142, further enhance the wicking process. The edge defining opening 140 is also preferably sharp.

A sharp edge 134 between a distal surface 136 at the distal portion of sidewall 130 and a surface 132 of the sidewall provide wicking when the airway adapter is in an inverted position. A similar sharp edge 157 is provided on provided on sidewall 150. These features for the airway adaptor present invention enable the adapter of this invention to be substantially less likely to become occluded by a liquid, solid, or mixture thereof regardless of the orientation of the airway adapter than is achieved by conventional airway adapters.*

Figure 5:
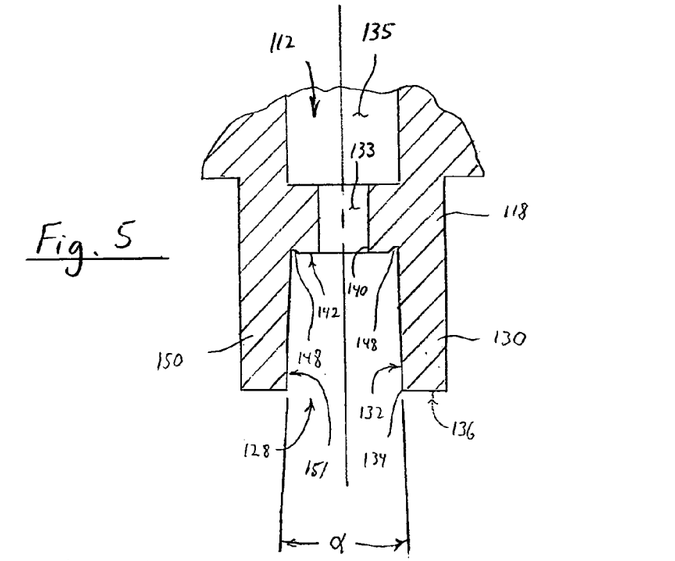
FIG. 5 is a side, cross-sectional view of the distal end portion of the protrusion in the airway adapter of FIG. 2.
Figure 6:
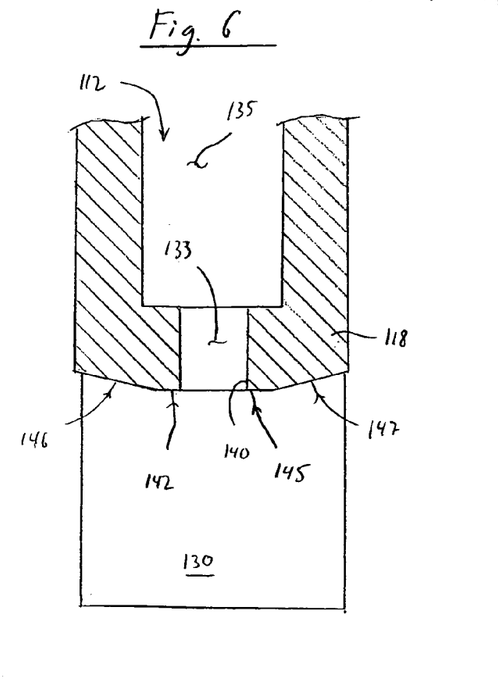
FIGS. 6 and 7 are front cross-sectional views illustrating alternative exemplary embodiments for the distal end portion of the protrusion in the airway adapter of the present invention.

As shown in FIG. 5, the inside walls defining U-shaped channel 128 are tapered away from the orifice. That is, the inside wall that generally are parallel to one another are also tapered such that a distance between these wall decreases in a direction from distal surface 136 to surface 142. The taper of walls 132 is indicated by angles α between lateral wall 132 on sidewall 130 and lateral wall 151 on sidewall 150. The present invention contemplates that angle α can range from 0–15°. However, in a preferred embodiment angle α is 5°.

FIG. 5 also illustrates channels 148 defined at the junction between lateral surfaces 132 and 151 of sidewalls 130 and 150 and surface 142 located at a bottom of U-shaped channel 128. This channel also enhances wicking. It is to be understood that the present invention contemplates eliminating channels 148 and providing a sharp angle between these surfaces.

Figure 7:
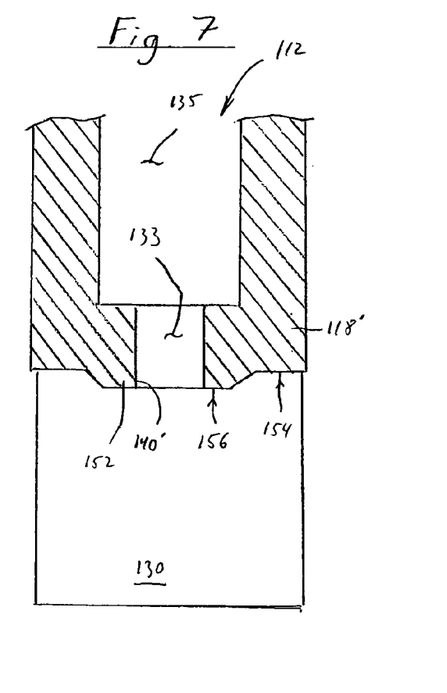

FIG. 7 illustrates an alternative exemplary embodiment for distal end portion 118' of the protrusion defined by the insert in the airway adapter. In this exemplary embodiment of the present invention, a small protrusion 152 is positioned around opening 140 at the base of the U-shaped channel. That is, distal end portion 118' includes a first surface 154 that is generally parallel to the direction of the flow of gas through the first passage, and a raised surface 156 extending from the first surface. Opening 140' to second gas flow passage 112 is defined in the raised surface.

FIGS. 8–11 illustrate a single piece pediatric/adult airway adapter 200 according to the principles of the present invention. Airway adapter 200 is similar in many respects to airway adapter 100 shown in FIGS. 2–7 and described above. The main difference is in the configuration for a protrusion 227 coupled to a tubular body 220. In the previous embodiment, the protrusion was defined by an attachable insert. In the embodiment of FIGS. 8–11, the protrusion is integral with the tubular body. Otherwise, the configuration for a distal end portion 218 of protrusion 227, and the alternative embodiments thereof, are substantially the same as the previous embodiment. For example, the distal end portion of protrusion 227 is positioned within tubular body and is spaced apart from the interior wall of the tubular body, and includes the sidewall wicking features discussed above.

Tubular body 220 that includes a first end portion 222 that is sized and configured to connect to a Y-connector in a ventilator circuit, and a second end portion 224 that is sized and configured to connect to an endotracheal tube connector. An outlet coupling 226 is integral with tubular body 220 generally at a midpoint along the length of the tubular body and extends from an exterior wall of the body. Outlet coupling 226 is generally aligned with protrusion 227, which is also integrally formed with the tubular body. The outlet coupling provides a structure 228 for connecting gas sampling conduit 32 to the airway adapter. More specifically, in this embodiment, an end portion of the gas sampling conduit is inserted into a proximal end portion 226 of a second gas flow passage 212, which is in fluid communication with a first gas flow passage 225 defined through the tubular body. In one exemplary embodiment, the outer surface of the gas sampling conduit is bonded to the inner surface of proximal end portion 226 to maintain the gas sampling conduit in an attached relation with the airway adapter. Of course, any conventional technique, such as a friction fitting, can be used to join the gas sampling conduit to the outlet coupling.

Second gas flow passage 212 is defined through outlet coupling 226 and protrusion 227. A distal end portion 218 of protrusion 227 includes sidewalls 230 and 260 extending therefrom. Sidewalls 230 and 260 include lateral surfaces 232 and 262 that generally face one anther and define the U-shaped channel. As in the previous embodiment, the junction between lateral surfaces 232 and 262 and a surface 242 in which an opening 240 to second gas flow passage 212 is defined, is a substantially sharp angle. For example, the preset invention contemplates that the angle between these lateral surfaces 232 and 262 and surface 242 is approximately 90°. Sidewalls 230 and 260 further include end surfaces 236 and 266. In an exemplary embodiment, end surfaces 236 and 266 are substantially planar surfaces and are also form at a substantially sharp right angle with respect to lateral surface 232 and 262. As in the previous embodiment, surface 242 can include inclined surfaces (See FIG. 6) or a raise surface (See FIG. 7) to provide additional resistance to ingress of fluid in to the second gas flow passage.

Protrusion 227 is preferably cylindrical in shape. While the present invention contemplates that other shapes, such as hexagonal, octagonal, etc., can be used for the protrusion, the substantially cylindrical shape provides an advantage in that the projection of the distal end portion of the protrusion into the gas stream denies physical support to particles or droplets of solids, liquids, or mixtures thereof, to the protrusion, increasing the likelihood that these particles or droplets break up and are moved away by the flow of the gas and do not enter the second gas flow passage.

Figure 12:
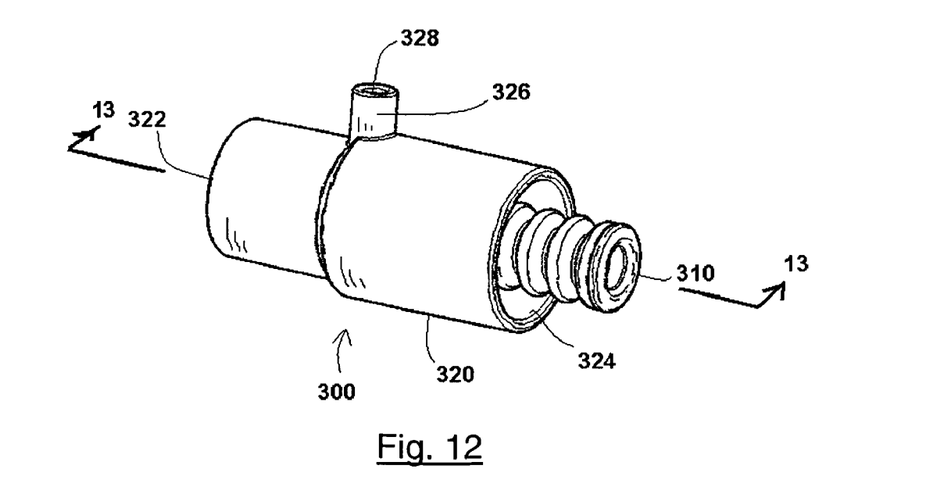
FIG. 12 is a perspective view of a single piece neonatal airway adapter according to the principles of the present invention.
Figure 13:
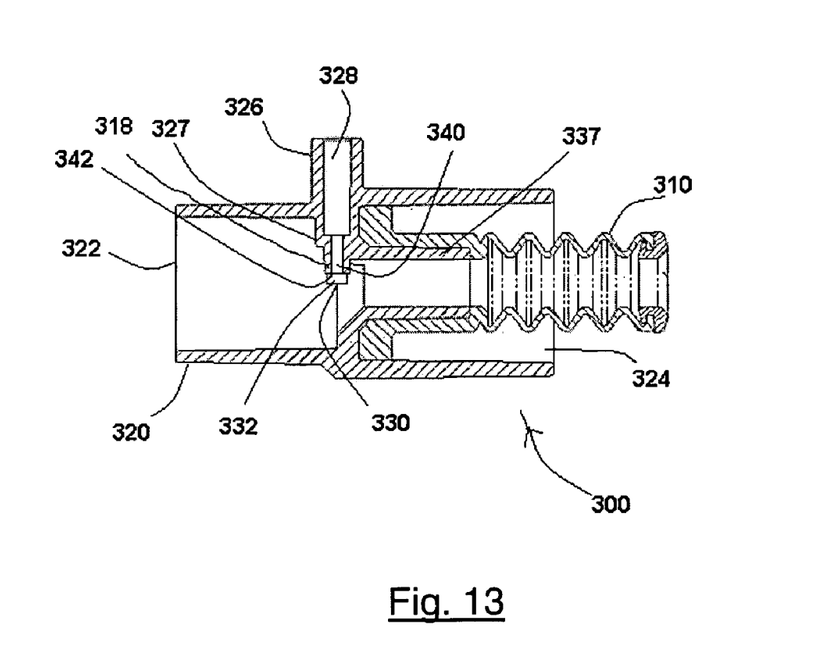
FIG. 13 is a cross-sectional longitudinal view of the single piece neonatal airway adapter along line 13—13 of FIG. 12.
Figure 14:
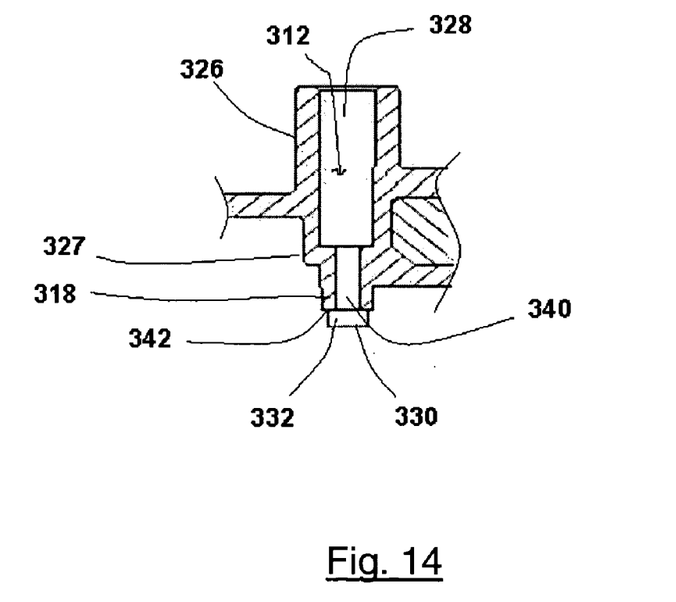
FIG. 14 is a detailed cross-sectional view of the distal end portion of the protrusion in the neonatal airway adapter of FIG. 12.

FIGS. 12–14 illustrate a single piece neonatal airway adapter 300 according to the principles of the present invention. Airway adapter 300 is similar in many respects to airway adapter 200 shown in FIGS. 8–11 and described above. For example, airway adapter 300 includes a protrusion 327 coupled to a tubular body 320 having first and second end portions 322 and 342. The main difference between the airway adapter of this embodiment and that of previous embodiments is the addition of a longitudinally compressible sleeve 310, which is adapted to mate with an endotracheal tube connector to reduce the deadspace between the sampling tube and endotracheal tube. Details of such a compressible sleeve, as well as alternative embodiments for the sleeve are disclosed in U.S. patent application Ser. No. 10/680,848 "Low Deadspace Airway Adapter" filed Oct. 7, 2003, the contents of which are incorporated herein by reference. In the illustrated exemplary embodiment, compressible sleeve 310 is mounted on an axial protrusion 337 that is coupled to the tubular body.

The configuration for a distal end portion 318 of protrusion 327, and the alternative embodiments thereof, are substantially the same as the previous embodiment. For example, the distal end portion of protrusion 327 is positioned within tubular body and is spaced apart from the interior wall of the tubular body, and includes the sidewall wicking features discussed above. Distal end portion 218 of protrusion 327 also includes sidewalls (only one sidewall 330 is illustrated) that define a U-shaped passage. An opening 340 to a second gas flow passage 312 is provided in a surface 342. The sidewalls include lateral surfaces (again, only lateral surfaced 332 is shown) that are disposed at a substantially sharp angle with a respect to surface 342 in which opening 340 is defined. As in the pediatric/adult airway adapter 200, the distal end surfaces of the sidewalls also form a substantially right angle with the lateral surfaces of the sidewall and a sharp angle is provided therebetween. As in the previous embodiment, surface 342 can include inclined surfaces (See FIG. 6) or a raise surface (See FIG. 7) to provide additional resistance to ingress of fluid in to the second gas flow passage.

An outlet coupling 326 is integral with tubular body 320 generally at a midpoint along the length of the tubular body and extends from an exterior wall of the body. Outlet coupling 326 is generally aligned with protrusion 327, which is also integrally formed with the tubular body. The outlet coupling provides a structure 328 for connecting gas sampling conduit 32 to the airway adapter as discussed above.

Figure 8:
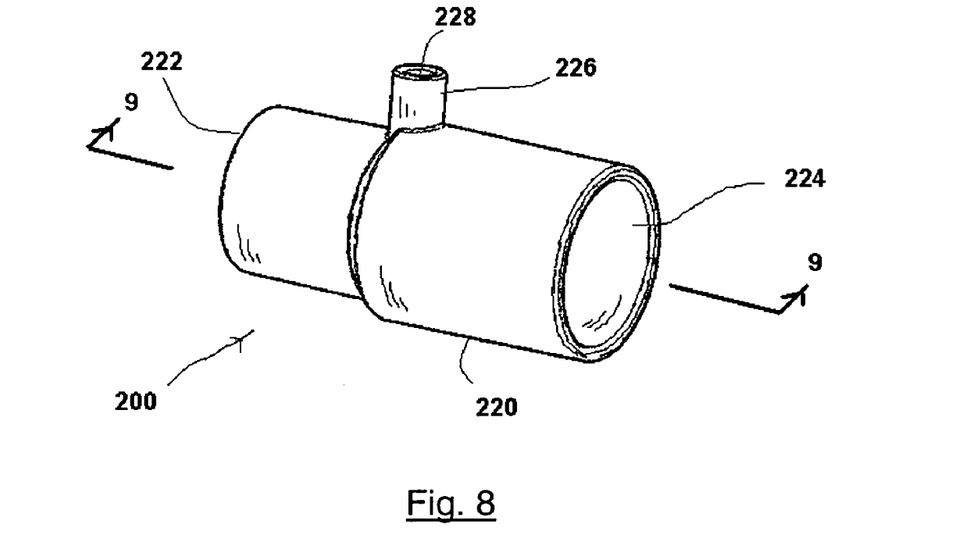
FIG. 8 is a perspective view of a single piece pediatric/adult airway adapter according to the principles of the present invention.
Figure 9:
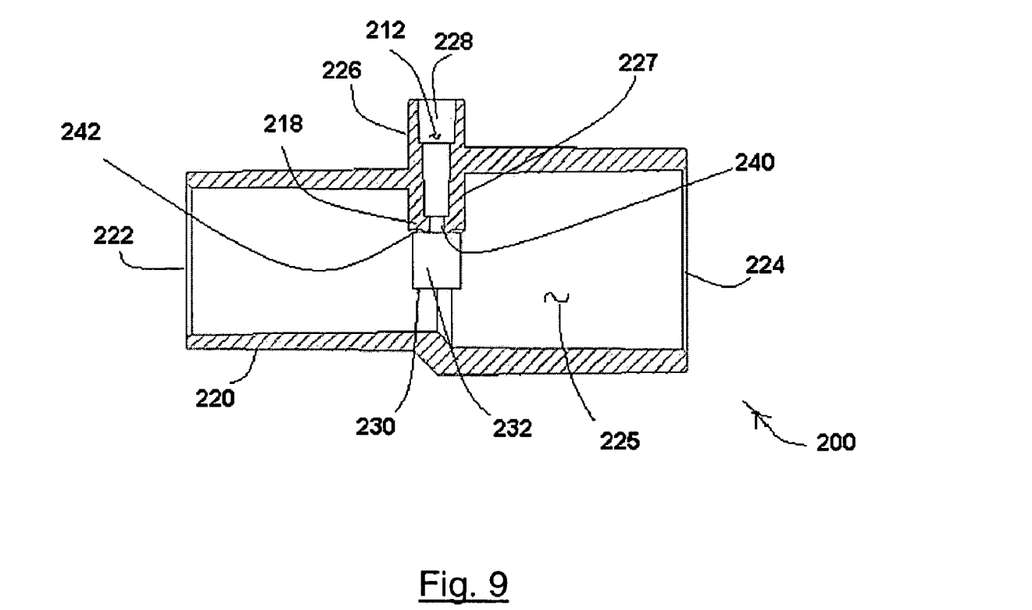
FIG. 9 is a cross-sectional view of the single piece pediatric/adult airway adapter taken along line 9—9 of FIG. 8.
Figure 10:
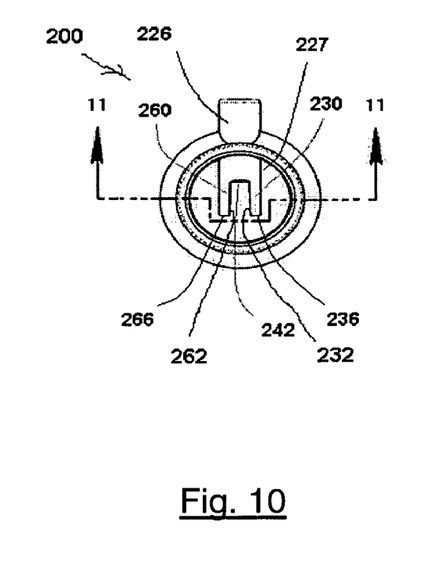
FIG. 10 is a side view of the single piece pediatric/adult airway adapter of FIG. 8.
Figure 11:
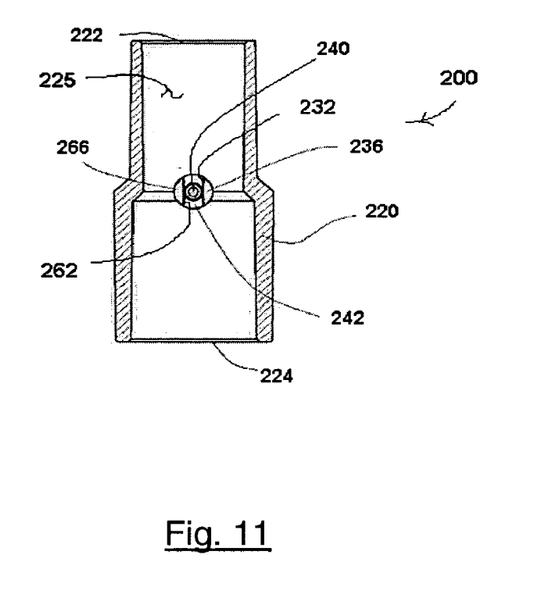
FIG. 11 is a cross-sectional view of the single piece pediatric/adult airway adapter along line 11—11 of FIG. 10.

Specific dimensions of the components of the illustrative airway adapters of the present invention are as follows. Protrusion 227 and 327, which are substantially tubular, are preferably about 5 mm long, i.e., when measured from the interior wall of the tubular body to the end of the sidewall on the distal end portion of the protrusion. The internal diameter of the openings 140, 240, or 340 is preferably about 1.2 mm. These dimensions provide for a smoother, relatively laminar flow of gas from the inlet opening into the gas sampling conduit, which typically has an internal diameter of 1 mm as, well as discourages the entrance of solids, liquids, and mixtures thereof into the second gas flow passage. The width of the sidewalls 230 and 260 in pediatric/adult airway adapter 200, is about 10 mm, whereas each sidewall has a height of about 5 mm. The width and height of the sidewalls of the neonatal/infant airway adapter 300 are about ⅓ the dimensions of the pediatric/adult version. In all embodiments shown, protrusion 227 and 327 and insert 110 are preferably formed from a hydrophobic material, which will resist contact with liquids and mixtures containing liquids.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An airway adaptor comprising:
   (a) a tubular body having a first gas flow passage defined therein and a longitudinal axis extending along the first gas flow passage; and
   (b) a protrusion extending from an interior wall of the tubular body into the gas flow passage, wherein the protrusion includes:
      (1) a distal end portion spaced apart from the interior wall of the tubular body, and wherein at least a first portion of the distal end portion is defined in a first plane that is generally parallel to the longitudinal axis, and
      (2) a second gas flow passage defined through the protrusion having an inlet defined in the first portion of the distal end portion, and an outlet at an exterior portion of the tubular body; and
   (c) a pair of sidewalls extending from the distal end portion of the protrusion such that each sidewall is defined in a second plane is generally parallel to the longitudinal axis, wherein the inlet of the second gas flow passage is disposed between the pair of sidewalls, and wherein the first plane is generally perpendicular to the second plane.

2. The airway adaptor of claim 1, wherein the protrusion is substantially tubular.

3. The airway adaptor of claim 1, wherein the protrusion is formed of substantially hydrophobic material.

4. The airway adaptor of claim 1, wherein the protrusion is substantially centrally located on the tubular body and extends into the first gas flow passage in a direction that is substantially perpendicular to the longitudinal axis.

5. The airway adapter of claim 1, wherein the protrusion is detachable from the tubular body.

6. The airway adapter of claim 1, wherein a channel is defined between the sidewalls, with the inlet of the second gas flow passage being located at a bottom of the channel.

7. The airway adapter of claim 1, wherein the second gas flow passage through the protrusion is defined by a plurality of bores having different diameters.

8. The airway adapter of claim 1, wherein each sidewall in the pair of sidewalls includes a substantially planar surface, and wherein the planar surfaces are oriented such that the planar surfaces face one another.

9. The airway adapter of claim 8, wherein the planar surfaces are tapered such that a distance between the planar surfaces decreases as a distance toward the distal end portion decreases.

10. The airway adapter of claim 1, wherein a channel is defined at a junction between each sidewall and a surface of the protrusion at the distal end portion.

11. The airway adapter of claim 1, wherein the distal end portion includes a first surface generally parallel to the direction of the flow of gas through the first passage and a raised surface extending from the first surface, and wherein the inlet is defined in the raised surface.

12. The airway adapter of claim 1, further comprising a coupling portion extending from an exterior wall of the tubular body adapted to be coupled to a conduit, and wherein the coupling portion includes a third gas flow passage in fluid communication with the second gas flow passage.

13. An airway adaptor comprising:
   (a) a tubular body having a first gas flow passage defined therein and a longitudinal axis extending along the first gas flow passage; and
   (b) a protrusion extending from an interior wall of the tubular body into the gas flow passage in a direction generally perpendicular to the longitudinal axis and terminating at a distal end portion that is spaced apart from the interior wall of the tubular body;
   (c) a second gas flow passage defined in the protrusion having an inlet at the distal end portion and an outlet at an exterior portion of the tubular body;
   (d) a first sidewall extending from a first side of the distal end portion of the protrusion in a cantilevered fashion, wherein the first sidewall extends from the protrusion in a direction that is generally perpendicular to the longitudinal axis; and
   (e) a second sidewall extending from a second side of the distal end portion of the protrusion in a cantilevered fashion, wherein the second sidewall extends from the protrusion in a direction that is generally perpendicular to the longitudinal axis, and wherein the inlet of the second gas flow passage is disposed between the pair of sidewalls.

14. The airway adapter of claim 13, wherein a channel is defined between the first sidewall and the second sidewalls with the inlet of the second gas flow passage being located at a bottom of the channel.

15. The airway adapter of claim 13, wherein the second gas flow passage through the protrusion is defined by a plurality of bores having different diameters.

16. The airway adapter of claim 13, wherein the first sidewall includes a first substantially planar surface, wherein the second sidewall includes a second substantially planar surface, and wherein the first planar surface and the second planar surface generally face one another.

17. The airway adapter of claim 16, wherein the first and the second planar surfaces are tapered such that a distance between the planar surfaces decreases as a distance toward the distal end portion decreases.

18. The airway adapter of claim 13, wherein the distal end portion includes a first surface generally parallel to the direction of the flow of gas through the first passage and a raised surface extending from the first surface, and wherein the inlet is defined in the raised surface.

19. The airway adapter of claim 13, further comprising:
a first channel defined at a first junction between the first sidewall and a surface of the protrusion at the distal end portion; and
a second channel defined at a second junction between the second sidewall and the surface of the protrusion at the distal end portion.

* * * * *